United States Patent [19]

Rajagopalan et al.

[11] 4,107,165

[45] Aug. 15, 1978

[54] TRIS[TETRAHYDROISOQUINOLINE] COMPOUNDS

[75] Inventors: Parthasarathi Rajagopalan, Westbury; Irwin J. Pachter, Woodbury, both of N.Y.

[73] Assignee: Endo Laboratories, Garden City, N.Y.

[21] Appl. No.: 723,336

[22] Filed: Sep. 15, 1976

Related U.S. Application Data

[60] Continuation of Ser. No. 561,435, Mar. 25, 1975, abandoned, which is a division of Ser. No. 336,973, Mar. 1, 1973, Pat. No. 3,928,611, which is a continuation of Ser. No. 165,346, Jul. 22, 1971, abandoned, which is a continuation-in-part of Ser. No. 1,029, Jan. 6, 1970, abandoned.

[51] Int. Cl.$^2$ .............................................. C07D 401/06
[52] U.S. Cl. ........................ 260/288 CE; 260/283 BZ; 260/283 CN; 260/287 D; 424/258
[58] Field of Search ................ 260/288 CE, 283 BZ, 260/282 CN, 287 D

[56] References Cited

U.S. PATENT DOCUMENTS

| | | | |
|---|---|---|---|
| 3,138,600 | 6/1964 | Fancher et al. ................ | 260/288 CE |
| 3,560,620 | 2/1971 | Schor et al. .................... | 260/288 CE |
| 3,667,488 | 6/1951 | Andersag et al. ............. | 260/283 BZ |
| 3,884,925 | 5/1975 | Buchner ......................... | 260/288 CE |
| 3,928,611 | 12/1975 | Rajagopalan et al. ............... | 424/258 |

*Primary Examiner*—Donald G. Daus
*Assistant Examiner*—Mary Vaughn

[57] ABSTRACT

Novel alkylenetris- and alkylenetetrakis-[1,2,3,4-tetrahydroisoquinoline] and -[3,4-dihydroisoquinoline] compounds, the pharmaceutically acceptable acid addition salts thereof and compositions containing such substances have been found useful for inhibiting the formation of blood clots in mammals and/or dissolving blood clots in mammals after they have been formed.

12 Claims, No Drawings

TRIS[TETRAHYDROISOQUINOLINE] COMPOUNDS

CROSS-REFERENCE TO OTHER APPLICATIONS

This is a continuation of Ser. No. 561,435, filed Mar. 25, 1975, now abandoned, which is a division of Ser. No. 336,973, filed Mar. 1, 1973, now U.S. Pat. No. 3,928,611, issued Dec. 23, 1975, which is a continuation of Ser. No. 165,346, filed July 22, 1971, now abandoned, which is a continuation-in-part of Ser. No. 1,029, filed Jan. 6, 1970, now abandoned.

BACKGROUND OF THE INVENTION

1. Field of the Invention

This invention relates to new compounds useful for inhibiting the formation of blood clots, or dissolving blood clots after they have been formed, and more particularly to novel alkylenetris- and alkylenetetrakis-[1,2,3,4-tetrahydroisoquinoline] and -[3,4-dihydroisoquinoline] compounds, and the pharmaceutically acceptable acid addition salts thereof.

2. Description of the Prior Art

In the formation of a blood clot, for example a thrombus, fibrinogen, a soluble plasma protein, is converted to the insoluble protein fibrin. As the fibrin is deposited it entraps blood cells within its meshwork to form a coagulum. In the case of a thrombus, the coagulum usually interferes with the flow through the blood vessel.

The defense of the living organism against such occurrence is the plasma protein called plasminogen which, under certain conditions, can be activated by an "activator" whereby the plasminogen is converted to the protein, plasmin. Plasmin possesses the property of efficiently digesting and destroying fibrin (fibrinolysis). The fibrinolysis results in dissolution of the clot, and, in the case of a thrombus, restores the patency of the vessel.

Under normal conditions, the organism has low levels of "activator" in the blood stream. It is believed that small amounts of plasminogen are constantly undergoing conversion to plasmin by the action of the "activator". However, from a quantitative viewpoint, the amount of activator normally present in insufficient to produce enough plasmin to lyse the relatively large amount of fibrin present in a clot such as a thrombus.

Fibrinolytic activity in vitro is manifested by many compounds such as the aromatic sulfonic acids, derivatives of salicylic acid, long chain fatty acids and halogenated unsaturated acids. Such compounds have not, however, been found to exhibit in vivo fibrinolytic or thrombolytic activity.

Fibrinolytic activity in vivo can be induced by nicotinic acid, procaine, phenylbutazone, acetylcholine, epinephrine, serotonin and histamine. However, the effect of these compounds is of short-lived duration, i.e., of the order of minutes.

Some sulphonylureas and steroids can induce an increase in fibrinolytic activity, but a lag period of the order of hours precedes the slow increase in lytic activity. Compounds of this type cannot be used when a substance is employed to effect thrombolytic therapy, because in such instance the activity must be rapidly induced to be effective in dissolving clots.

Streptokinase, a streptococcal protein, has been used for thrombolysis, but the side effects of pyrogenicity and anaphylactic reactions have limited its use.

Urokinase, a protein isolated from human urine, has also been used for thrombolysis but the difficulties involved in accumulating large supplies of the starting material, human urine, and the great cost of preparing the substance has proscribed its general and practical utility.

Bacterial pyrogens have also been used to effect thrombolysis, but the severity and unpredictability of the pyrogenic reactions have negated their usefulness.

SUMMARY OF THE INVENTION

The present invention provides compounds which inhibit the formation of blood clots (by inhibiting platelet aggregation and/or fibrin formation) or dissolve such clots as they are formed (by fibrinolysis) or after they have been formed (by fibrinolysis). Such substances demonstrate activity in mammals in vivo, are highly potent, long-lasting, rapid in onset, readily prepared and suffer fron none of the difficulties associated with materials of natural origin.

Various of the compounds of this invention may be used to effect fibrinolysis of the clot in acute thrombosis. Many possess the further advantage of oral activity and may be employed prophylactically to maintain increased fibrinolytic activity on a long term basis and thus diminish the incidence of new thrombotic episodes.

Other objects and advantages of the compounds disclosed in the present application, methods of preparing them and compositions containing the same which are useful in preventing the formation of blood clots, or in effecting high sustained levels of fibrinolytic activity in mammals without toxic effect, even at substantially high dosage levels, will be apparent from the following detailed description of the preferred embodiments thereof.

The novel compounds according to the invention are characterized by the following general formula:

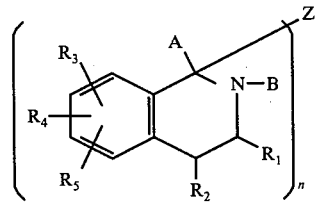

wherein

A and B is each hydrogen or, taken together, represent an additional carbon to nitrogen bond;

$R_1$ and $R_2$ represent hydrogen or lower alkyl;

$R_3$, $R_4$ and $R_5$ represent hydrogen, lower alkyl, halogen, hydroxy, lower alkoxy, lower alkenoxy, lower alkynoxy, lower acyloxy, aryloxy or phenyl lower alkoxy. $R_3$ and $R_4$ or $R_4$ and $R_5$ may be linked to form a lower alkylenedioxy. By the term "lower" alkyl, alkoxy, etc., is meant such groups having from 1 to about 6 carbon atoms, except for "lower" alkylenedioxy, which refers to alkylenedioxy having up to 3 carbon atoms;

Z represents an organic radical having a valence of n, said radical being a hydrocarbon group that can contain up to four hetero atoms selected from the group consisting of oxygen, sulfur, and nitrogen, and wherein said radical can contain up to three substituents selected from the group consisting of amino, nitro, halo, hydroxy, lower alkyl, lower alkoxy, benzyloxy, trifluoromethyl, and a lower alkylenedioxy;

$n$ represents the numbers 3 or 4.

This invention is also characterized by pharmaceutically acceptable acid addition salts of the compounds of the above general formula as well as compositions containing such substances. The term "pharmaceutically acceptable addition salt" includes such salts as: the mineral acid salts, e.g., the hydrochloride, hydrobromide, sulfate and phosphate; and organic acid salts such as the lactate, tartrate, citrate, succinate, benzoate, acetate, p-toluenesulfonate and benzenesulfonate, and others conventionally formed from acids conventionally used in the pharmaceutical art.

The alkylenetris- or alkylenetetrakis-[1,2,3,4-tetrahydroisoquinoline] compounds within the above formula are useful as fibrinolytic agents in mammals. Such materials additionally possess the property of inhibiting platelet aggregation and may thus be utilized for inhibiting the formation of blood clots as well as for dissolving such clots as they may be formed or after they have been formed. The alkylenetris- or alkylenetetrakis-[3,4-dihydroisoquinoline] compounds within the above formula are intermediates in the preparation of the corresponding tetrahydroisoquinoline compounds and, moreover, possess the property of inhibiting platelet aggregation. Thus, both the tetrahydroisoquinoline and dihydroisoquinoline compounds within the above formula are useful for inhibiting the formation of blood clots.

The compounds of the invention are prepared by permitting selected tri- and tetracarboxylic acids or their derivatives (esters, and chlorides and the like) to react with appropriately substituted phenethylamines. The tri- and tetraphenethylamides thus derived are cyclized through dehydration to the 3,4-dihydroisoquinoline compounds within the above formula, in accordance with the Bischler-Napieralski synthesis* with which those skilled in the art are familiar. The cyclization is effected by reacting the amides with phosphorus oxychloride ($POCl_3$) by itself or diluted with an equal amount of a suitable solvent, e.g., benzene or toluene. The dihydroisoquinolines thus produced are thereafter converted to the 1,2,3,4-tetrahydroisoquinoline compounds of the above formula by reduction. The reduction step is carried out employing, for example, sodium borohydride in alcoholic solution or lithium aluminum hydride in tetrahydrofuran.

* See, for instance, Whaley et al, Organic Reactions VI, 74 (1951); and Bergstrom, Chem. Revs. 35, 218 (1944).

It will be apparent from a consideration of the chemistry involved in making the products of this invention that their preparation results in the formation of mixtures of diastereoisomers. It has been found that all such isomers display fibrinolytic or platelet aggregation inhibiting activity. The preceding formula therefore embraces all of the isomers arising during the synthesis of these compounds. The designation of the compounds of the formula, by names and by formulas throughout the specification and claims, shall be read to include all isomers and mixtures thereof. The preparation of any particular stereoisomer from a mixture of such isomers will be within the competence of one skilled in the art. A typical technique involves reacting the mixture of isomers of any given compound with a particular stereoisomer of an optically-active acid to form an isomeric mixture of acid addition salts. These salts will have differing physical properties and can be separated by known means.

Oxygenated functions are generally beneficial for maximum clot-dissolving activity and with one preferred aspect of this invention there is included in $R_3$, $R_4$ and $R_5$ one or more lower alkoxy functions such as methoxy, isopropoxy, butoxy, or a methylenedioxy. These functions are most effective when situated at the 6 and 7 positions of the tetrahydroisoquinoline rings.

The Z variable represents, in most cases, the residue after removal of the carboxy groups of the tri- or tetracarboxylic acid that was used to produce the compound of the invention. Representative types of organic groups that can be the Z variable include alkanetriyl, alkanetetrayl, alkanetriyl having from 1 to 3 oxygen, sulfur, or nitrogen hetero atoms, phenylalkanetriyl, benzylalkanetriyl and substituted benzylalkanetriyl, alkanetetrayl having from 1 to 4 oxygen, sulfur or nitrogen atoms, cycloalkanediylidenetetraethylene, tetrahydrothiopyrandiylidenetetraethylene, tetrahydropyrandiylidenetetraethylene, and the like. In addition, the Z variable can contain substituents such as amino, nitro, halo, hydroxy, lower alkyl, lower alkoxy, benzyloxy, trifluoromethyl, and a lower alkylenedioxy. In most cases, the Z variable will contain from 5 to 18 carbon atoms.

Thus, the Z chain connecting the tetrahydroisoquinoline and dihydroisoquinoline groups in the above formula may vary within wide limits with retention of potency. Activity is maximized, however, when the individual isoquinoline moieties are separated by chains of from three to ten carbon atoms. The nature of Z is determined by the tri- and tetracarboxylic acids or their derivatives (esters, acid chlorides and the like) used in the synthesis of the compounds within the generic formula. Representative of acids which may be used in the preparation of biologically potent compounds of the above class are the following:

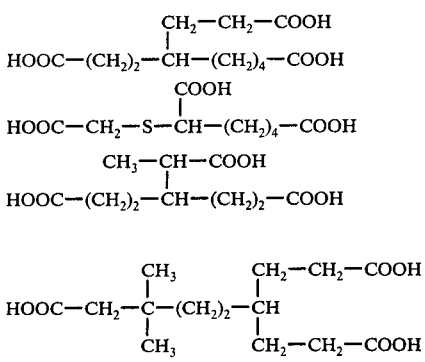
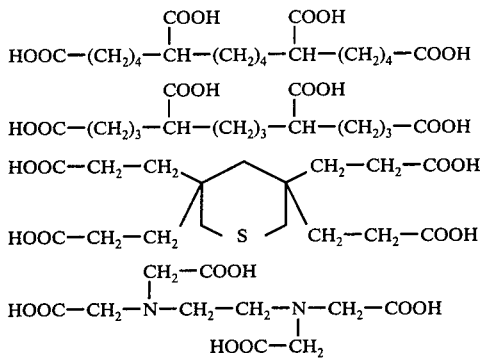

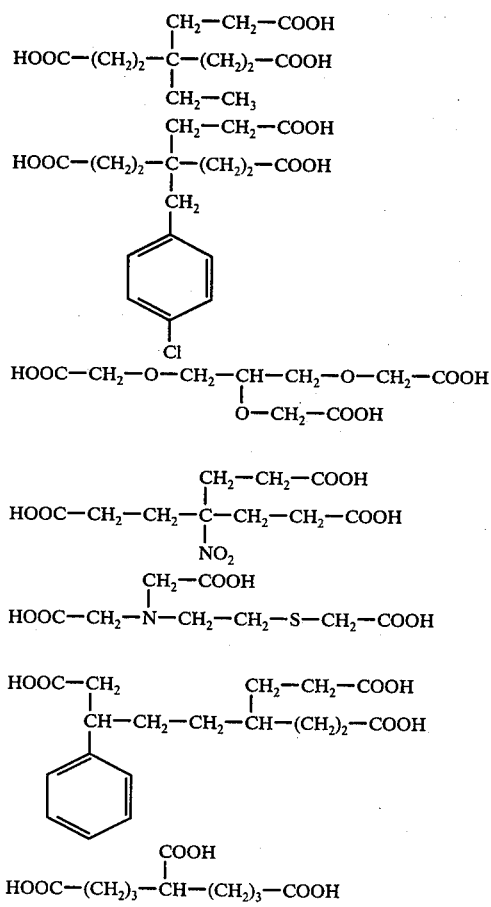
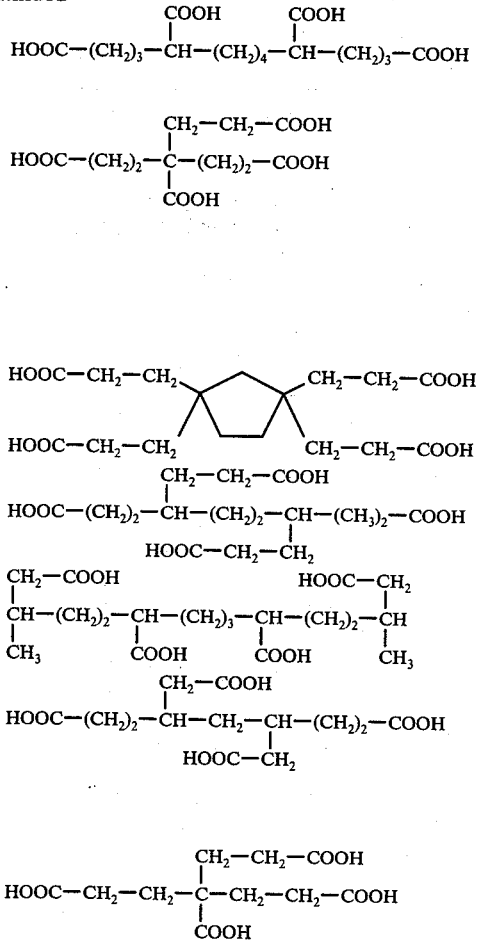

PREFERRED EMBODIMENTS OF THE INVENTION

Within the broad claims of the fibrinolytically active 1,2,3,4-tetrahydroisoquinoline compounds of the invention, there are several preferred classes of compounds. Such preferred classes include the following:

I. Tris[1,2,3,4-tetrahydro-1-isoquinolinyl]alkanes, wherein the alkane moiety has from 5 to 18 carbon atoms and wherein the tetrahydroisoquinoline moieties can be unsubstituted or can be substituted with lower alkyl, lower alkoxy, lower alkylenedioxy, benzyloxy, or hydroxy groups.

II. Tetrakis[1,2,3,4-tetrahydro-1-isoquinolinyl]alkanes, wherein the alkane moiety has from 7 to 18 carbon atoms and wherein the tetrahydroisoquinoline moieties can be unsubstituted or can contain lower alkyl, lower alkoxy, lower alkylenedioxy, benzyloxy or hydroxy substituents.

III. 1,1'-{1-[(1,2,3,4-Tetrahydro-1-isoquinolinylmethyl)thio]pentanemethylene}bis[1,2,3,4-tetrahydroisoquinolines] and 1,1'-{1-[(1,2,3,4-tetrahydro-1-isoquinolinylmethyl)oxy]pentamethylene}bis[1,2,3,4-tetrahydroisoquinolines], wherein the tetrahydroisoquinoline moieties can be unsubstituted or can have lower alkyl, lower alkoxy, lower alkylenedioxy, benzyloxy or hydroxy substituents. These compounds can be produced by first reacting a 3-bromo-2-oxocyclohexanecarboxylic acid ester with a glycolic acid ester or thioglycolic acid ester to produce a 3-(carboxymethyl)oxy-(or thio)-2-oxocyclohexanecarboxylic acid di-ester. This latter compound is reacted with sodium hydroxide, water and ethanol to form a tri-ester of 2-(carboxymethyl)oxy-(or thio)-heptanedioic acid. (The reaction involved here is the known "acid" hydrolysis of a betaketo ester). The tricarboxylic acid ester is then reacted with an appropriate phenethylamine in a Bischler-Napieralski synthesis, followed by reduction to produce the compounds of the invention.

IV. 1,1'-{3-Benzyl-3-[2-(1,2,3,4-tetrahydro-1-isoquinolinyl)ethyl]pentamethylene}bis[1,2,3,4-tetrahydroisoquinolines] wherein the benzyl moiety can be unsubstituted or can contain up to three lower alkyl, lower alkoxy, halo (fluoro, chloro, bromo, or iodo), trifluoromethyl, or a lower alkylenedioxy substituent on the benzene ring, and wherein the tetrahydroisoquinoline moieties can be unsubstituted or can contain lower alkyl, lower alkoxy, lower alkylenedioxy, benzyloxy, or hydroxy substituents. These compounds are prepared by first cyanoethylating an appropriately substituted acetophenone (the substituents, if any, are on the phenyl group of the acetophenone) to produce a 3-benzoyl-3-(2-cyanoethyl)-1,5-pentanedicarbonitrile. The trinitrile is hydrolyzed to produce a 4-benzoyl-4-(2-carboxyethyl)-heptanedioic acid. After a Wolff-Kishner reduction (to change the benzoyl group to a benzyl group), the triacid is esterified and then reacted with a phenethylamine, cyclized, and reduced to the compounds of the invention.

V. 1,1',1'',1'''-(1,3-Cycloalkanediylidenetetraethylene)tetrakis[1,2,3,4-tetrahydroisoquinolines], wherein the cycloaliphatic ring contains from 5 to 8 carbon atoms, and wherein the tetrahydroisoquinoline moieties can be unsubstituted, or can contain lower alkyl, lower alkoxy, lower alkylenedioxy, benzyloxy, or hydroxy substituent.

VI. 1,1',1'',1'''-(3,5-Tetrahydrothiopyrandiylidenetetraethylene)tetrakis[1,2,3,4-tetrahydroisoquinolines] and 1,1',1'',1'''-(3,5-tetra hydropyrandiylidenetetraethylene)tetrakis[1,2,3,4-tetrahydroisoquinolines], wherein the isoquinoline moieties can be unsubstituted or can contain lower alkyl, lower alkoxy, lower alkylenedioxy, benzyloxy, or hydroxy substituents.

VII. 1,1',1''-(Nitrilotrialkylene)tris[1,2,3,4-tetrahydroisoquinolines], wherein each alkylene individually contains from 1 to 3 carbon atoms, and wherein the tetrahydroisoquinoline moieties can be unsubstituted or can contain lower alkyl, lower alkoxy, lower alkylenedioxy, benzyloxy, or hydroxy substituents.

VIII. 1,1',1'',1'''-[Alkylenedinitrilotetra(alkylene')-]tetrakis[1,2,3,4-tetrahydroisoquinolines], wherein alkylene contains from 2 to 8 carbon atoms, and each alkylene' individually contains 1 or 2 carbon atoms, and wherein the tetrahydroisoquinoline moieties can be unsubstituted or can contain lower alkyl, lower alkoxy, lower alkylenedioxy, benzyloxy, or hydroxy substituents. These would include such compounds as 1,1',1'',1'''-(ethylenedinitrilotetramethylene)tetrakis[1,2,3,4-tetrahydroisoquinolines], 1,1',1'',1'''-(tetramethylenedinitrilotetraethylene)tetrakis[1,2,3,4-tetrahydroisoquinolines], and 1,1',1'',1'''-(ethylenedinitrilo-N,N'-diethylene-N,N'-dimethylene)tetrakis[1,2,3,4-tetrahydroisoquinolines].

The corresponding 3,4-dihydroisoquinoline compounds are also preferred in accordance with the present invention.

From a consideration of the foregoing discussion, it is apparent that there are a wide variety of compounds that are within the scope of the above formula. In said formula, the several variables $R_1$ – $R_5$ and Z can be any of a wide variety of groups. For instance, specific representative $R_1$ and $R_2$ groups include hydrogen, methyl, ethyl, propyl, hexyl, and the like. Illustrative $R_3$, $R_4$ and $R_5$ groups are hydrogen, methoxy, ethoxy, butoxy, hexyloxy, methyl, ethyl, isopropyl, butyl, pentyl, hexyl, chloro, bromo, iodo, fluoro, allyloxy, 2-butenyloxy, 2-propynyloxy, acetoxy, phenoxy, benzyloxy, methylenedioxy, ethylenedioxy, trimethylenedioxy, hydroxy, and the like.

An outstanding feature of the compounds of this invention is their relative lack of toxicity. Although they are active at very low dose levels, it is possible to exceed minimum effective levels by wide margins without encountering serious adverse reactions. This permits the compounds to be used within wide limits without concern about undesirable side effects, as are so frequently encountered upon inadvertent overdosage of other substances of great potency. For example, by intraperitoneal administration to rats, 1,1'-{3-[2-(1,2,3,4-tetrahydro-6,7-dimethoxy-1-isoquinolinyl)ethyl]heptamethylene}bis[1,2,3,4-tetrahydro-6,7-dimethoxyisoquinoline] trihydrochloride, a compound within the above generic formula, was found to be effective in inducing fibrinolysis at 0.01 mg./kg. and at 10 mg./kg. (a 1000-fold difference in dose) without producing toxicity.

Certain representative compounds within the scope of the present invention have been tested for fibrinolytic activity by the whole blood clot lysis method, as modified from the procedure of Billimoria et al.[1] In this method, blood from rats given a fibrinolytic compound intraperitoneally is taken and diluted 1:10. A standard amount is clotted with thrombin, incubated at 37° C for four hours, and the amount of clot that has lysed is determined. The $ED_{50}$ dose of a compound is that amount, in mg/kg, which will cause the lysis of 50% of the clot under the above conditions. These $ED_{50}$ values for the various compounds tested are set forth in the following table, each of the compounds being identified by name and by the number of the ensuing example in which its synthesis is described. As basis for comparison, the value of bisobrin (EN-1661, 1,1'-tetramethylenebis[1,2,3,4-tetrahydro-6,7-dimethoxyisoquinoline], meso isomer)[2] in this test is shown at the end of the table.

[1] Billimoria, J. D., Drysdale, J., James, D. C., Maclagan, N. F., Lancet II, 471 (1959)
[2] Schor, J. M.: Chemical Control of Fibrinolysis-Thrombolysis. New York, Wiley-Interscience, 1970, pp. 113-34 (cf. fig. 4.7, p. 123)

| FIBRINOLYTIC ACTIVITY OF COMPOUNDS OF THE INVENTION | | |
| --- | --- | --- |
| Example No. | Compound Name | $ED_{50}$ |
| 1.1 | 1,1'-{3-[2-(1,2,3,4-tetrahydro-6,7-dimethoxy-1-isoquinolinyl)ethyl]heptamethylene}bis[1,2,3,4-tetrahydro-6,7-dimethoxyisoquinoline] trihydrochloride | 0.02 |
| 2.1 | 1,1',1'',1'''-(1,4,8,11-undecatetrayl)-tetrakis[1,2,3,4-tetrahydro-6,7-dimethoxyisoquinoline] tetrahydrochloride | 0.03 |
| 5.1 | 1,1'-{3,6-bis[2-(1,2,3,4-tetrahydro-6,7-dimethoxy-1-isoquinolinyl)ethyl]octamethylene}bis[1,2,3,4-tetrahydro-6,7-dimethoxyisoquinoline] tetrahydrochloride | 0.06 |
| 6.1 | 1,1'-{1-[(1,2,3,4-tetrahydro-6,7-dimethoxy-1-isoquinolinylmethyl)thio]-pentamethylene}bis[1,2,3,4-tetrahydro-6,7-dimethoxyisoquinoline] trihydrochloride | <0.6 |
| 7.1 | 1,1'-{2-phenyl-5-[2-(1,2,3,4-tetrahydro-6,7-dimethoxy-1-isoquinolinyl)ethyl]-heptamethylene}bis[1,2,3,4-tetrahydro-6,7-dimethoxyisoquinoline] trihydrochloride | <0.1 |
| 8.1 | 1,1'-{2,2-dimethyl-5-[2-(1,2,3,4-tetrahydro-6,7-dimethoxy-1-isoquinolinyl)-ethyl]heptamethylene}bis[1,2,3,4-tetrahydro-6,7-dimethoxyisoquinoline] trihydrochloride | <0.4 |
| 10.1 | 1,1'-{3-[2-(1,2,3,4-tetrahydro-6-methoxy-1-isoquinolinyl)ethyl]heptamethylene}bis[1,2,3,4-tetrahydro-6-methoxyisoquinoline] trihydrochloride | 0.5 |
| 15.1 | 1,1',1'',1'''-(1,5,10,14-tetradecanetetrayl)tetrakis[1,2,3,4-tetrahydro-6,7-dimethoxyisoquinoline] tetrahydrochloride | 0.04 |
| 16.1 | 1,1',1'',1'''-(1,4,9,12-dodecanetetrayl)-tetrakis[1,2,3,4-tetrahydro-6,7-dimethoxyisoquinoline] tetrahydrochloride | 0.03 |
| 17.1 | 1,1',1''-[1,2,3-propanetriyltri(oxyethylene)-tris[1,2,3,4-tetrahydro-6,7-dimethoxyisoquinoline] trihydrochloride | 0.8 |
| 17.3 | 1,1',1''-(nitrilotriethylene)tris[1,2,3,4-tetrahydro-6,7-dimethoxyisoquinoline] trihydrochloride | 0.7 |
| 18.1 | 1,1'-{3-nitro-3-[2-(1,2,3,4-tetrahydro-6,7-dimethoxy-1-isoquinolinyl)ethyl]-pentamethylene}bis[1,2,3,4-tetrahydro-6,7-dimethoxyisoquinoline] trihydrochloride | <0.6 |
| 19.1 | 1,1',1''-(1,4,7-heptanetriyl)tris[1,2,3,4-tetrahydro-6,7-dimethoxyisoquinoline] trihydrochloride | 0.03 |
| Standard | bisobrin dihydrochloride | 0.5 |

Another selection of representative compounds within the scope of the present invention, including some listed in the previous table, have been tested for their ability to inhibit platelet aggregation. Citrated whole blood from human volunteers, who had not taken any medicine for the previous week, was centrifuged to obtain platelet rich plasma. On addition of ADP (adenosine diphosphate) to this platelet rich plasma, incubated at 37° C with constant stirring, in an aggregometer, optical density changes can be observed which are caused by platelet aggregation. Thus, the extent of ADP-induced platelet aggregation is determined for each sample of blood used. Compounds to be tested were incubated for five minutes prior to the addition of ADP. The $ED_{50}$ of a compound is that amount, in $\gamma/ml$, which reduces platelet aggregation by 50% under the above conditions. These $ED_{50}$ values for the various compounds are listed in the table below, each of the compounds again being identified by name and by the number of the example in which its synthesis is described. As standard for comparison, the value of dipyridamole (Persantin, 2,2',2'',2'''-[(4,8-dipiperidinopyrimido[5,4-d]pyrimidine-2,6-diyl)dinitrilo]tetraethanol), a clinically used coronary vasodilator, generally recognized as being effective against ADP-induced platelet aggregation and experimental thrombosis[3], is listed at the end of the table.

[3] Didisheim, P., Bowie, E. J., Owen, C. A., Mayo Clin. Proc. 45, 51 (1970)

PLATELET AGGREGATION INHIBITORY ACTIVITY OF COMPOUNDS OF THE INVENTION

| Example No. | Compound Name | $ED_{50}$ |
|---|---|---|
| 1.1 | 1,1'-{3-[2-(1,2,3,4-tetrahydro-6,7-dimethoxy-1-isoquinolinyl)ethyl]heptamethylene}bis[1,2,3,4-tetrahydro-6,7-dimethoxyisoquinoline] trihydrochloride | 6 |
| 1.1a | 1,1'-{3-[2-(3,4-dihydro-6,7-dimethoxy-1-isoquinolinyl)ethyl]heptamethylene}bis[3,4-dihydro-6,7-dimethoxyisoquinoline] trihydrochloride | <40 |
| 7.1a | 1,1'-{5-[2-(3,4-dihydro-6,7-dimethoxy-1-isoquinolinyl)ethyl]-2-phenylheptamethylene}bis[3,4-dihydro-6,7-dimethoxyisoquinoline] trihydrochloride | <40 |
| 15.1a | 1,1',1'',1'''-(1,5,10,14-tetradecanetetrayl)tetrakis[3,4-dihydro-6,7-dimethoxyisoquinoline] tetrahydrochloride | 27 |
| 17.1a | 1,1',1''[1,2,3-propanetriyltri(oxyethylene)]tris[3,4-dihydro-6,7-dimethoxyisoquinoline] trihydrochloride | <40 |
| 18.1 | 1,1'-{3-nitro-3-[2-(1,2,3,4-tetrahydro-6,7-dimethoxy-1-isoquinolinyl)ethyl]-pentamethylene}bis[1,2,3,4-tetrahydro-6,7-dimethoxyisoquinoline] trihydrochloride | 9 |
| 18.1a | 1,1'-{3-[2-(3,4-dihydro-6,7-dimethoxy-1-isoquinolinyl)ethyl]-3-nitropentamethylene}bis[3,4-dihydro-6,7-dimethoxyisoquinoline] trihydrochloride | 6 |
| 19.1a | 1,1',1''-(1,4,7-heptanetriyl)tris[3,4-dihydro-6,7-dimethoxyisoquinoline] trihydrochloride | <40 |
| Standard | dipyridamole | 270 |

The compounds of this invention are also active by intravenous, intramuscular, oral and rectal administration.

The compositions of this invention contain a compound of the above formula or a non toxic acid addition salt thereof together with a carrier. The carrier may be either a solid or liquid and the dry filled capsules, dragees, pills, aqueous solutions, non-aqueous solutions, jellies, suppositories, syrups, suspensions, sprays, powders, and the like. The compositions can, and in many cases do, contain suitable preservatives, coloring and flavoring agents. Some examples of the carriers which can be used in the preparation of the products of the invention are gelatin capsules, sugars such as lactose and sucrose; cellulose, methyl cellulose and cellulose acetate phthalate; gelatin; talc; magnesium stearate; vegetable oils such as peanut oil, cottonseed oil, sesame oil, olive oil, corn oil and oil of theobroma; liquid petrolatum, polyethylene glycol; glycerine, sorbitol; propylene glycol; ethanol; agar; water and isotonic saline.

In preparing the compositions of the invention for pharmaceutical uses, the conventional practices and precautions are used. The compositions intended for parenteral administration must be sterile and this can be accomplished either by using sterile ingredients and carrying out the production under aseptic conditions or by sterilizing the final composition by one of the usual procedures such as millipore filtration. Customary care should be exercised that no incompatible condition exists between the active component and the diluent preservative or flavoring agent or in the conditions employed in preparation of the compositions.

The compositions of the invention can be introduced into the mammal by the oral, rectal, or parenteral route. This can be done by injecting the liquid preparations intravenously, intramuscularly, intraperitoneally, or subcutaneously; by swallowing, in the cases of the solid and liquid preparations, by local application to the mucous membranes, in the case of jellies, suppositories, tablets and the like; by inhalation of sprays or mists of the liquid preparations and the like.

The invention is illustrated by the following non-limiting examples in which all temperatures specified are in degrees centigrade, and in which decomposition temperatures are identified by ("dec.") as appropriate.

EXAMPLE 1

1,1'-{3-[2-(1,2,3,4-TETRAHYDRO-6,7-DIMETHOXY-1-ISOQUINOLINYL)ETHYL]HEPTAMETHYLENE}BIS[1,2,3,4-TETRAHYDRO-6,7-DIMETHOXYISOQUINOLINE] TRIHYDROCHLORIDE TRIHYDRATE

A mixture of 100 g. of the trimethyl ester of 4-(2-carboxyethyl)nonanedioic acid and 210 g. of 3,4-dimethoxyphenethylamine is stirred and heated at 180°–200° for 5 hours under an atmosphere of nitrogen, cooled to about 50° and dissolved in 1 l. of chloroform. The solution is washed thrice with 800 ml. portions of 1:1 hydrochloric acid, then with water, dried over anhydrous magnesium sulfate and filtered. The filtrate is stripped of the solvent under reduced pressure, the residue dissolved in a minimum quantity of acetone and the solution is added, with stirring, to an excess of anhydrous ether cooled in dry ice. The resulting triamide which separates is filtered and melts at 101°–103° after recrystallization from ethanol.

A mixture of 100 g. of the amide and 400 ml. of phosphorus oxychloride diluted with an equal volume of anhydrous benzene is refluxed, protected from moisture, for 5 hours, cooled, and evaporated to dryness under reduced pressure. The residue is carefully hydrolyzed with water and the clear solution thus obtained is extracted once with 500 ml. of chloroform. The chloroform extract is discarded, the aqueous layer is cooled and neutralized with 50% aqueous sodium hydroxide, and then extracted thrice with 800 ml. portions of chloroform. The combined chloroform extracts are thoroughly washed with water, dried over anhydrous magnesium sulfate and filtered. The filtrate is stripped of the solvent under reduced pressure, the residue (1.1a) dissolved in 500 ml. of absolute ethanol and treated with 13.5 g. of sodium borohydride, added in small portions, with vigorous stirring. The mixture is then refluxed, protected from moisture, for 5 hours, cooled, and evaporated to dryness under reduced pressure. The residue is treated with about a liter of water and extracted thrice with 800 ml. portions of benzene. The combined benzene extracts are washed thoroughly with water, dried over anhydrous magnesium sulfate and filtered. The residue obtained from the filtrate after removal of the solvent under reduced pressure is dissolved in minimum quantity of anhydrous benzene and the solution added, with agitation, to 1 l. of absolute ether saturated with dry hydrogen chloride. The salt that separates is filtered rapidly, washed repeatedly with anhydrous ether, air-dried, dissolved in the requisite quantity of pure chloroform and added with stirring to an excess of anhydrous ether. The solid thus obtained is filtered rapidly, washed thoroughly with anhydrous ether and dried in a vacuum desiccator, to yield (1.1) the title compound, m.p. 175°–198° (dec.).

To purify the intermediate (1.1a), the crude residue obtained after stripping off the chloroform is converted to the hydrochloride, in ether, and the resulting salt taken up in chloroform. Precipitation with ether, followed by two further reprecipitations from chloroform solution by either yields (1.1a) 1,1'-{3-[2-(3,4-dihydro-6,7-dimethoxy-1-isoquinolinyl)ethyl]heptamethylene}·bis[3,4-dihydro-6,7-dimethoxyisoquinoline] trihydrochloride trihydrate, as a yellow solid, m.p. 130–150° (dec.).

When, in the above procedure for the preparation of 1.1, the 3,4-dimethoxyphenethylamine is replaced by an equimolar amount of
  4-allyloxy-3-methoxyphenethylamine
  3,4,5-trimethoxyphenethylamine
  3,4-dimethoxy-α-methylphenethylamine
  3,4-dimethoxy-β-methylphenethylamine
  3,4-dimethoxy-α,β-dimethylphenethylamine
  3-ethoxy-2-isopropoxyphenethylamine
  4-butoxy-3-methoxy-α-methylphenethylamine
  m-methylphenethylamine
  m-chlorophenethylamine
  2,3-dimethylphenethylamine
  2,3-dimethoxyphenethylamine
respectively, following products are obtained:
(1.2): 1,1'-{3-[2-(7-allyloxy-1,2,3,4-tetrahydro-6-methoxy-1-isoquinolyl)ethyl]heptamethylene}bis[7-allyloxy-1,2,3,4-tetrahydro-6-methoxyisoquinoline] trihydrochloride trihydrate
(1.3): 1,1'-{3-[2-(1,2,3,4-tetrahydro-6,7,8-trimethoxy-1-isoquinolinyl)ethyl]heptamethylene}bis[1,2,3,4-tetrahydro-6,7,8-trimethoxyisoquinoline] trihydrochloride trihydrate
(1.4): 1,1'-{3-[2-(1,2,3,4-tetrahydro-6,7-dimethoxy-3-methyl-1-isoquinolinyl)ethyl]heptamethylene}·bis[1,2,3,4-tetrahydro-6,7-dimethoxy-3-methylisoquinoline] trihydrochloride trihydrate
(1.5): 1,1'-{3-[2-(1,2,3,4-tetrahydro-6,7-dimethoxy-4-methyl-1-isoquinolinyl)ethyl]heptamethylene]-bis[1,2,3,4-tetrahydro-6,7-dimethoxy-4-methylisoquinoline] trihydrochloride trihydrate
(1.6): 1,1'-{3-[2-(1,2,3,4-tetrahydro-6,7-dimethoxy-3,4-dimethyl-1-isoquinolinyl)ethyl]heptamethylene}·bis[1,2,3,4-tetrahydro-6,7-dimethoxy-3,4-dimethylisoquinoline] trihydrochloride trihydrate
(1.7): 1,1'-{3-[2-(6-ethoxy-1,2,3,4-tetrahydro-5-isopropoxy-1-isoquinolinyl)ethyl]heptamethylene}bis[6-ethoxy-1,2,3,4-tetrahydro-5-isopropoxyisoquinoline] trihydrochloride trihydrate
(1.8): 1,1'-{3-[2-(7-butoxy-1,2,3,4-tetrahydro-6-methoxy-1-isoquinolinyl)ethyl]heptamethylene}·bis[7-butoxy-1,2,3,4-tetrahydro-6-methoxyisoquinoline] trihydrochloride trihydrate
(1.9): 1,1'-{3-[2-(1,2,3,4-tetrahydro-6-methyl-1-isoquinolinyl)ethyl]heptamethylene}bis[1,2,3,4-tetrahydro-6-methylisoquinoline] trihydrochloride trihydrate
(1.10): 1,1'-{3-[2-(6-chloro-1,2,3,4-tetrahydro-1-isoquinolinyl)ethyl]heptamethylene}bis[6-chloro-1,2,3,4-tetrahydroisoquinoline] trihydrochloride trihydrate
(1.11): 1,1'-{3-[2-(1,2,3,4-tetrahydro-5,6-dimethyl-1-isoquinolinylethyl]heptamethylene}bis[1,2,3,4-tetrahydro-5,6-dimethylisoquinoline] trihydrochloride trihydrate
(1.12): 1,1'-{3-[2-(1,2,3,4-tetrahydro-5,6-dimethoxy-1-isoquinolinylethyl]heptamethylene}bis[1,2,3,4-tetrahydro-5,6-dimethoxyisoquinoline] trihydrochloride trihydrate

EXAMPLE 2

1,1',1'',1'''-(1,4,8,11-UNDECANETETRAYL)TETRAKIS[1,2,3,4-TETRAHYDRO-6,7-DIMETHOXYISOQUINOLINE] TETRAHYDROCHLORIDE TETRAHYDRATE

To a freshly prepared solution of 54 g. of sodium methoxide in 1 l. of anhydrous methanol, 156 g. of a commercially available mixture of the methyl and ethyl esters of 2-oxocyclopentanecarboxylic acid is added, with stirring, in a rapid stream, followed, after 5 minutes, by the addition of 101 g. of 1,3-dibromopropane. The mixture is stirred and refluxed for 14 hours, cooled and filtered, and the residue washed with ether. The combined filtrates are stripped of the solvents under reduced pressure, the residue is treated with water, and then extracted twice with ether. The combined ether extracts are washed with water, dried over anhydrous magnesium sulfate and filtered. The liquid obtained by removal of the solvent from the filtrate under reduced pressure is distilled under vacuum. Tetramethyl 1,4,5,11-undecanetetracarboxylate is collected at 215°–220°/0.5 mm.

A mixture of 36.4 g. of this tetraester and 90 g. of 3,4-dimethoxyphenethylamine is heated, with stirring, at 180°–200° for 5 hours in an atmosphere of nitrogen, cooled to about 50°, and added to 500 ml. of chloroform. The resulting solution is washed thrice with 600 ml. portions of 1:1 hydrochloric acid, then with water and dried over anhydrous magnesium sulfate and filtered. The filtrate is stripped of the solvent under reduced pressure and the residue dissolved in methanol and added to a large excess of anhydrous ether. The product separates as a sticky solid which is filtered, washed with anhydrous ether and air-dried.

Of the amorphous tetramide thus obtained, 28 g. are mixed with 110 ml. of phosphorous oxychloride and refluxed for 5 hours. The residue obtained by evaporation of the mixture to dryness under reduced pressure is treated carefully with water, and the resulting clear solution is extracted twice with 400 ml. of chloroform. The chloroform extracts are discarded and the aqueous layer is cooled, rendered strongly alkaline with 50% aqueous sodium hydroxide and extracted thrice with 300 ml. portions of chloroform. The combined chloroform extracts are washed thoroughly with water, dried over anhydrous magnesium sulfate and filtered. The filtrate is stripped of the solvent under reduced pressure, the residue dissolved in 100 ml. of absolute ethanol and treated with 5 g. of sodium borohydride, added in small portions, with stirring. The mixture, protected from moisture, is refluxed for 5 hours with stirring, and then evaporated to dryness under reduced pressure. The residue is treated with 500 ml. of water and extracted thrice with 300 ml. portions of benzene. The combined benzene extracts are washed thoroughly with water, dried over anhydrous magnesium sulfate and filtered. The residue left on removal of the solvent from the filtrate under reduced pressure is dissolved in minimum quantity of anhydrous benzene and added to 500 ml. of anhydrous ether saturated with anhydrous hydrogen chloride. (2.1) 1,1',1'',1'''-(1,4,8,11-Undecanetetrayl)tetrakis[1,2,3,4-tetrahydro-6,7-dimethoxyisoquinoline] tetrahydrochloride tetrahydrate thus obtained, after purification by dissolution in a minimum quantity of methanol, followed by reprecipitation by an excess of anhydrous ether, melts at 180°–212° (dec.) (sint. at 75°)

EXAMPLE 3

1,1',1'',1'''-(3,5-TETRAHYDROTHIOPYRAN-DIYLIDENETETRAETHYLENE)TETRAKIS[1,2,3,4-TETRAHYDRO-6,7-DIMETHOXYISOQUINOLINE] TETRAHYDROCHLORIDE TETRAHYDRATE

To a stirred solution of 23.2 g. of tetrahydro-4H-thiopyran-4-one in 250 ml. of dioxane maintained at 50°, 4 ml. of a 40% methanolic solution of N-benzyltrimethylammonium hydroxide (Triton B) are added, followed, after five minutes, by rapid dropwise addition of 45 g. of acrylontrile. The temperature of the mixture rises to 85°–90° within a few minutes and crystals start to separate. On completion of addition the mixture is stirred for 30 minutes, diluted with 250 ml. of methanol, filtered, and the solid washed with methanol and ether. The 4-oxothiopyrandiylidenetetrapropionitrile thus obtained melts at 222°–225°, and is pure enough for the next step.

To a solution of 76 g. of sodium hydroxide and 760 ml. of water, 133 g. of this oxotetrapropionitrile are added, the mixture is stirred and refluxed vigorously for 20 hours, and filtered to remove any undissolved impurities. The filtrate is cooled and acidified with conc. hydrochloric acid. Cooling the mixture in an icebath with vigorous scratching furnishes colorless crystals of the corresponding oxothiopyrantetrapropionic acid, which are filtered, washed thoroughly with water and air-dried. Recrystallization from a mixture of tetrahydrofuran and hexane yields the pure product, m.p. 186°–188°.

A 3 l. pressure bomb is charged with 54 g. of powdered sodium hydroxide, dispersed in 200 ml. of absolute ethanol, 35 ml. of 100% hydrazine hydrate, and a solution of 83 g. of the oxothiopyrantetrapropionic acid in 500 ml. of hot absolute ethanol, the bomb is closed and heated at 190°–210° for 18 hours. It is then cooled and the nitrogen formed during the reaction is released carefully. The supernatant alcoholic solution is removed and evaporated to dryness under reduced pressure. The sodium salts left in the bomb are dissolved in minimum quantity of water and added to the residue obtained by evaporation of the alcoholic solution. The resulting clear solution is cooled, acidified with concentrated hydrochloric acid and extracted thrice with 500 ml. portions of chloroform. The combined chloroform extracts are dried over anhydrous magnesium sulfate, filtered and stripped of the solvent under reduced pressure. The residue is dissolved in 200 ml. of anhydrous methanol saturated with dry hydrogen chloride, left at room temperature overnight and stripped of the solvent and hydrogen chloride. The residue is dissolved in 800 ml. of ether and the solution is washed with saturated aqueous sodium bicarbonate, then with water, dried over anhydrous magnesium sulfate and filtered. The filtrate is stripped of the solvent under reduced pressure and the residual liquid distilled under vacuum. Tetramethyl 3,5-tetrahydrothiopyrandiylidenetetrapropionate is collected at 220°–250°/0.3–0.4 ml.

Following the procedure outlined in Example 1, the tetraester is converted into the tetramide by heating with 3,4-dimethoxyphenethylamine, the tetramide cyclized with phosphorus oxychloride, and the tetrakis dihydroisoquinoline thus obtained is reduced, without purification, with sodium borohydride to yield (3.1) 1,1',1'',1'''-(3,5-tetrahydrothiopyrandiylidenetetraethylene)tetrakis[1,2,3,4-tetrahydro-6,7-dimethoxyisoquinoline], isolated as its tetrahydrochloride tetrahydrate, m.p. 190°–200° (dec.)

Pyrophoric nickel is prepared by washing commercial Raney nickel several times in absolute ethanol, and then refluxing the centrifuged solids for three hours in absolute ethanol. A mixture of 20 g. of this nickel and 2 g. of 1,1', 1'',1'''-(3,5-tetrahydrothiopyrandiylidenetetraethylene)tetrakis[1,2,3,4-tetrahydro-6,7-dimethoxyisoquinoline] tetrahydrochloride is refluxed for two days in 70% ethanol. The mixture is centrifuged, the liquid decanted from the nickel, which is washed twice with hot ethanol and once with water, and the combined washings are evaporated to dryness under reduced pressure. The residue is worked up as in Example 1 to yield (3.2) 1,1'-{3,5-dimethyl-3,5-bis[2-(1,2,3,4-tetrahydro-6,7-dimethoxy-1-isoquinolinyl)ethyl]heptamethylene}bis[1,2,3,4-tetrahydro-6,7-dimethoxyisoquinoline], isolated as its tetrahydrochloride.

Following the same sequence of steps outlined above for 3.1, but using tetrahydro-4H-pyran-4-one in place of the tetrahydro-4H-thiopyran-4-one, (3.3) 1,1',1'',1'''-(3,5-tetrahydropyrandiyldenetetraethylene)tetrakis[1,2,3,4-tetrahydro-6,7-dimethoxy-1-isoquinoline] is prepared and isolated as its tetrahydrochloride.

EXAMPLE 4

1,1',1'',1'''-(1,3-CYCLOPENTANEDIYLIDENETETRAETHYLENE)TETRAKIS[1,2,3,4-TETRAHYDRO-6,7-DIMETHOXYISOQUINOLINE] TETRAHYDROCHLORIDE TETRAHYDRATE

A mixture of 185 g. of 2-oxo-1,3-cyclopentanediylidenetetra propionic acid, 1 liter of absolute ethanol, 100 g. of powdered sodium hydroxide and 65 ml. of 100% hydrazine hydrate is heated in a pressure bomb at 190°–210° for 18 hours. The bomb is opened carefully to release the nitrogen formed during the course of the reaction, the supernatant solution decanted and evaporated to dryness under reduced pressure. The sodium salts left in the bomb are dissolved in a minimum quantity of water and the solution added to the residue mentioned above. The resulting clear solution is cooled, acidified with concentrated hydrochloric acid and extracted thrice with 800 ml. portions of ether. The combined ether extracts are dried over anhydrous magnesium sulfate and filtered. The filtrate on evaporation to dryness under reduced pressure yields a viscous liquid which solidifies on standing to give 1,3-cyclopentanediylidenetetrapropionic acid, which is recrystallized from a mixture of benzene and hexane.

A solution of 178 g. of the tetracarboxylic acid, dissolved in 600 ml. of anhydrous methanol, is treated carefully with 40 ml. of conc. sulfuric acid, with agitation, refluxed for 15 hours and then stripped of the solvent in vacuo. The residue is treated with crushed ice and water and extracted thrice with 600 ml. portions of ether. The combined ether extracts are washed successively with water, saturated aqueous sodium bicarbonate and water, dried over anhydrous magnesium sulfate and filtered. Removal of the solvent from the filtrate under reduced pressure yields a liquid which is distilled under vacuum. Tetramethyl 1,3-cyclopentanediylidenetetrapropionate distills over at 240°–245°/0.8–0.9 mm. and solidifies on standing. After trituration with n-pentane, it melts at 50°–52°.

The ester is converted through the series of reactions outlined in Example 1 to (4.1) 1,1′,1″,1‴-(1,3-cyclopentanediylidenetetraethylene)tetrakis[1,2,3,4-tetrahydro-6,7-dimethoxyisoquinoline] tetrahydrochloride tetrahydrate, m.p. 223°–228° (dec.).

When, in the above procedure, the 3,4-dimethoxyphenethylamine is replaced by an equimolar amount of
  m-methoxyphenethylamine
  4-benzyloxy-3-methoxyphenethylamine
  3,4-methylenedioxyphenethylamine
  3,4-diethoxyphenethylamine
  β-methyl-3,4-methylenedioxyphenethylamine
  3,4-dimethylphenethylamine
  phenethylamine
respectively, the following products are obtained:
(4.2): 1,1′,1″,1‴-(1,3-cyclopentanediylidenetetraethylene)tetrakis[1,2,3,4-tetrahydro-6-methoxyisoquinoline] tetrahydrochloride tetrahydrate
(4.3): 1,1′,1″,1‴-(1,3-cyclopentanediylidenetetraethylene)tetrakis[7-benzyloxy-1,2,3,4-tetrahydro-6-methoxyisoquinoline] tetrahydrochloride tetrahydrate
(4.4): 1,1′,1″,1‴-(1,3-cyclopentanediylidenetetraethylene)tetrakis[1,2,3,4-tetrahydro-6,7-methylenedioxyisoquinoline] tetrahydrochloride tetrahydrate
(4.5): 1,1′,1″,1‴-(1,3-cyclopentanediylidenetetraethylene)tetrakis[6,7-diethoxy-1,2,3,4-tetrahydroisoquinoline] tetrahydrochloride tetrahydrate
(4.6): 1,1′,1″,1‴-(1,3-cyclopentanediylidenetetraethylene)tetrakis[1,2,3,4-tetrahydro-4-methyl-6,7-methylenedioxyisoquinoline] tetrahydrochloride tetrahydrate
(4.7): 1,1′,1″,1‴-(1,3-cyclopentanediylidenetetraethylene)tetrakis[1,2,3,4-tetrahydro-6,7-dimethylisoquinoline] tetrahydrochloride tetrahydrate
(4.8): 1,1′,1″,1‴-(1,3-cyclopentanediylidenetetraethylene)tetrakis[1,2,3,4-tetrahydroisoquinoline] tetrahydrochloride tetrahydrate Reduction of 4.3 with hydrogen over 10% palladium on charcoal in acetic acid gives rise to (4.9) 1,1′,1″,1‴-(1,3-cyclopentanediylidenetetraethylene)tetrakis[1,2,3,4-tetrahydro-6-methoxy-7-isoquinolinol], isolated as its tetrahydrochloride tetrahydrate.

When a 2 g. portion of 4.1 is heated in 20 g. of 48% hydrobromic acid containing 0.2 g. of 50% hypophosphorus acid until no more hydrogen chloride or methyl bromide is evolved, the demethylated product (4.10) 1,1′,1″,1‴-(1,3-cyclopentanediylidenetetraethylene)tetrakis[1,2,3,4-tetrahydro-6,7-isoquinolinediol], isolated as its tetrahydrobromide tetrahydrate, is obtained. By the same procedure, demethylation of 4.2 yields (4.11) 1,1′,1″,1‴-(1,3-cyclopentanediylidenetetraethylene)tetrakis[1,2,3,4-tetrahydro-6-isoquinolinol] tetrahydrobromide tetrahydrate.

EXAMPLE 5

1,1′-{3,6-BIS[2-(1,2,3,4-TETRAHYDRO-6,7-DIMETHOXY-1-ISOQUINOLINYL)ETHYL]OCTAMETHYLENE}BIS[1,2,3,4-TETRAHYDRO-6,7-DIMETHOXYISOQUINOLINE] TETRAHYDROCHLORIDE TETRAHYDRATE

A mixture of 34.6 g. of 4,7-bis(2-carboxyethyl)decanedioic acid and 72.4 g. of 3,4-dimethoxyphenethylamine is heated at 180°–200° for 5 hours in an atmosphere of nitrogen. The mixture is then cooled and dissolved in chloroform. The resulting solution is washed thrice with 300 ml. portions of 1:1 hydrochloric acid, then with water and then dried over anhydrous magnesium sulfate. Filtration and removal of the solvent from the filtrate under reduced pressure yields a solid which is recrystallized from ethanol. The tetramide thus obtained melts at 148°–150°.

The amide is converted by the procedure described in Example 1 to (5.1) 1,1′-{3,6-bis[2-(1,2,3,4-tetrahydro-6,7-dimethoxy-1-isoquinolinyl)ethyl]-octamethylene}•bis[1,2,3,4-tetrahydro-6,7-dimethoxyisoquinoline] tetrahydrochloride tetrahydrate, m.p. 210°–215° (dec.), via (5.1a) 1,1′-{3,6-bis[2-(3,4-dihydro-6,7-dimethoxy-1-isoquinolinyl)ethyl]octamethylenebis[3,4-dihydro-6,7-dimethoxyisoquinoline], isolated as a light yellow tetrahydrochloride tetrahydrate, m.p. 218°–220° (dec.) after two recrystallizations from isopropanol.

Replacing the 3,4-dimethoxyphenethylamine in the above procedure for the preparation of 5.1 by an equimolar amount of:
  2,5-dimethoxyphenethylamine
  4-benzyloxy-3-methoxyphenethylamine
  3-methoxy-4-phenoxyphenethylamine
  m-ethoxyphenethylamine
  3-methoxy-4-methylphenethylamine
  2-chloro-3,4-dimethoxyphenethylamine
respectively, gives rise to the following products:
(5.2): 1,1′-{3,6-bis[2-(1,2,3,4-tetrahydro-5,8-dimethoxy-1-isoquinolyl)ethyl]octamethylene}bis[1,2,3,4-tetrahydro-5,8-dimethoxyisoquinoline] tetrahydrochloride tetrahydrate
(5.3): 1,1′-{3,6-bis[2-(7-benzyloxy-1,2,3,4-tetrahydro-6-methoxy-1-isoquinolinyl)ethyl]octamethylene}bis[7-benzyloxy-1,2,3,4-tetrahydro-6-methoxyisoquinoline] tetrahydrochloride tetrahydrate
(5.4): 1,1′-{3,6-bis[2-(1,2,3,4-tetrahydro-6-methoxy-7-phenoxy-1-isoquinolinyl)ethyl]octamethylene}•bis[1,2,3,4-tetrahydro-6-methoxy-7-phenoxyisoquinoline] tetrahydrochloride tetrahydrate
(5.5): 1,1′-{3,6-bis[2-(6-ethoxy-1,2,3,4-tetrahydro-1-isoquinolinylethyl]octamethylene}bis[6-ethoxy-1,2,3,4-tetrahydroisoquinoline] tetrahydrochloride tetrahydrate
(5.6): 1,1′-{3,6-bis[2-(1,2,3,4-tetrahydro-6-methoxy-7-methyl-1-isoquinolinyl)ethyl]octamethylene}•bis[1,2,3,4-tetrahydro-6-methoxy-7-methylisoquinoline] tetrahydrochloride tetrahydrate
(5.7): 1,1′-{3,6-bis[2-(5-chloro-1,2,3,4-tetrahydro-6,7-dimethoxy-1-isoquinolinyl)ethyl]octamethylene}•bis[5-chloro-1,2,3,4-tetrahydro-6,7-dimethoxyisoqinoline] tetrahydrochloride tetrahydrate Debenzylation of 5.3 by the method of 4.9 gives rise to (5.8) 1,1'-{3,6-bis[1,2,3,4-tetrahydro-7-hydroxy-6-methoxy-1-isoquinolinyl)ethyl]octamethylene}-bis[1,2,3,4-tetrahydro-6-methoxy-7-isoquinolinol], isolated as its tetrahydrochloride tetrahydrate.

Demethylation of 5.2 and 5.6 respectively by the method of 4.11, gives rise to the following products:
(5.9): 1,1'-{3,6-bis[2-(1,2,3,4-tetrahydro-5,8-dihydroxy-1-isoquinolinyl)ethyl]octamethylene}bis[1,2,3,4-tetrahydro-5,8-isoquinolinediol] tetrahydrochloride tetrahydrate
(5.10): 1,1'-{3,6-bis[2-(1,2,3,4-tetrahydro-6-hydroxy-7-methyl-1-isoquinolinyl)ethyl]octamethylene}•bis[1,2,3,4-tetrahydro-7-methyl-6-isoquinolinol] tetrahydrochloride tetrahydrate

EXAMPLE 6

1,1'-{1-[(1,2,3,4-TETRAHYDRO-6,7-DIMETHOXY-1-ISOQUINOLINYLMETHYL)THIO]PENTAMETHYLENE}BIS[1,2,3,4-TETRAHYDRO-6,7-DIMETHOXYISOQUINOLINE] TRIHYDROCHLORIDE TRIHYDRATE

A solution of 72 g. of ethyl thioglycolate in 30 ml. of absolute ethanol is added to a stirred, freshly prepared solution of 17.5 g. of sodium ethoxide in 200 ml. of absolute ethanol. After 10 minutes the mixture is cooled to −20°, stirred in an atmosphere of nitrogen and treated with 150 g. of ethyl 3-bromo-2-oxocyclohexanecarboxylate in 60 ml. of absolute ethanol, added dropwise. After the addition of the bromo ester is complete, the mixture is stirred at room temperature for 2 hours and filtered. The residue is washed with anhydrous ether and the combined filtrates are stripped of ethanol and ether under reduced pressure. The residue is treated with water and extracted twice with 500 ml. portions of ether. The combined ether extracts are washed with water, dried over anhydrous magnesium sulfate and filtered. Removal of the solvent from the filtrate under reduced pressure yields 3-[(carboxymethyl)thio]-2-oxocyclohexanecarboxylic acid diethyl ester, which is collected by vacuum distillation at 190°–200°/0.3 mm.

A mixture of 250 g. of sodium hydroxide, 200 ml. of water and 150 ml. of ethanol is heated at 50° for 30 minutes in an atmosphere of nitrogen and then treated with a solution of 100 g. of the above ester in 50 ml. of ethanol in the course of 30 minutes. After the addition is complete the mixture is heated at 50°, in an atmosphere of nitrogen, for 5 hours, and stripped of the solvent under reduced pressure. The residue is treated with ice and water, acidified and extracted thrice with 300 ml. portions of chloroform. The combined chloroform extracts are dried over anhydrous magnesium sulfate and filtered. The filtrate, on being stripped of the solvent under reduced pressure, yields a viscous liquid which is dissolved in 150 ml. of absolute ethanol, and the alcoholic solution is saturated with dry hydrogen chloride and refluxed for 30 minutes. Removal of the solvent and hydrogen chloride under reduced pressure furnishes a liquid which is distilled under vacuum. 2-[(Carboxymethyl)thio]heptanedioic acid triethyl ester is collected at 208°–212°/0.3–0.4 mm.

Following the procedure described in Example 1, 11 g. of the ester thus obtained on being heated with 25 g. of 3,4-dimethoxyphenethylamine, yields the corresponding triamide which, without purification, is cyclized with phosphorus oxychloride. The product is reduced with sodium borohydride to yield (6.1) 1,1'-[1-[(1,2,3,4-tetrahydro-6,7-dimethoxy-1-isoquinolinylmethyl)thio]pentamethylene]bis[1,2,3,4-tetrahydro-6,7-dimethoxyisoquinoline], isolated as its trihydrochloride trihydrate, m.p. 125°–165° (dec.) (sint. at 100°).

EXAMPLE 7

1,1'-[2-PHENYL-5-[2-(1,2,3,4-TETRAHYDRO-6,7-DIMETHOXY-1-ISOQUINOLINYL)ETHYL]HEPTAMETHYLENE}-BIS[1,2,3,4-TETRAHYDRO-6,7-DIMETHOXYISOQUINOLINE] TRIHYDROCHLORIDE TRIHYDRATE

Following the procedure outlined in Example 1, 28 g. of 6-(2-carboxyethyl)-3-phenylnonanedioic acid trimethyl ester, b.p. 190°–195°/0.2 mm. on being heated with 47 g. of 3,4-dimethoxyphenethylamine yields the corresponding triamide, m.p. 71°–75°, which is cyclized with phosphorus oxychloride, and the resulting product (7.1a) reduced with sodium borohydride to yield (7.1) 1,1'-{2-phenyl-5-[2-(1,2,3,4-tetrahydro-6,7-dimethoxy-1-isoquinolinyl)ethyl]heptamethylene}bis[1,2,3,4-tetrahydro-6,7-dimethoxyisoquinoline], isolated as its trihydrochloride trihydrate, m.p. 190°–210° (dec.).

The intermediate 7.1a is purified in a manner very similar to that used to purify 1.1a, to yield (7.1a) 1,1'-{5-[2-(3,4-dihydro-6,7-dimethoxy-1-isoquinolinyl)ethyl]-2-phenylheptamethylene}bis[3,4-dihydro-6,7-dimethoxyisoquinoline] trihydrochloride trihydrate, a light yellow solid with a m.p. of 200°–210° (dec.)

EXAMPLE 8

1,1'-{2,2-DIMETHYL-5-[2-(1,2,3,4-TETRAHYDRO-6,7-DIMETHOXY-1-ISOQUINOLINYL)ETHYL]-HEPTAMETHYLENE}BIS[1,2,3,4-TETRAHYDRO-6,7-DIMETHOXYISOQUINOLINE] TRIHYDROCHLORIDE TRIHYDRATE

Following the procedure outlined in Example 1, 49.5 g. of 6-(2-carboxyethyl)-3,3-dimethylnonanedioic acid trimethyl ester, b.p. 145–155/0.7–0.9 mm., on being heated with 95 g. of 3,4-dimethoxyphenethylamine yields the corresponding triamide, m.p. 91°–93°, which is cyclized with phosphorus oxychloride, and the product obtained is reduced with sodium borohydride to yield (8.1) 1,1'-{2,2-dimethyl-5-[2-(1,2,3,4-tetrahydro-6,7-dimethoxy-1-isoquinolinyl)ethyl]heptamethylene}•bis[1,2,3,4-tetrahydro-6,7-dimethoxyisoquinoline], isolated as its trihydrochloride trihydrate, m.p. 190°–197° (dec.).

EXAMPLE 9

1,1'-{3-[2-(1,2,3,4-TETRAHYDRO-1-ISOQUINOLINYL)ETHYL]HEPTAMETHYLENE}BIS[1,2,3,4-TETRAHYDROISOQUINOLINE] TRIHYDROCHLORIDE TRIHYDRATE

Following the procedure outlined in Example 1, 57 g. of 4-(2-carboxyethyl)nonanedioic acid trimethyl ester on being heated with 92 g. of phenethylamine gives rise to the corresponding triamide, m.p. 118°–120°, which is cyclized with phosphorus oxychloride and the resulting product reduced with sodium borohydride to yield (9.1) 1,1'-{3-[2-(1,2,3,4-tetrahydro-1-isoquinolinyl)ethyl]heptamethylene}bis[1,2,3,4-tetrahydroisoquinoline], isolated as its trihydrochloride trihydrate, m.p. 140°–200° (dec.).

EXAMPLE 10

1,1'-{3-[2-(1,2,3,4-TETRAHYDRO-6-METHOXY-1-ISOQUINOLINYL)ETHYL]HEPTAMETHYLENE}BIS[1,2,3,4-TETRAHYDRO-6-METHOXYISOQUINOLINE] TRIHYDROCHLORIDE TRIHYDRATE

Following the method outlined in Example 1, 30 g. of 4-(2-carboxyethyl)nonanedioic acid trimethyl ester on being heated with 60 g. of m-methoxyphenethylamine yields the corresponding triamide, which is cyclized with phosphorus oxychloride and the product obtained is reduced with sodium borohydride to yield (10.1) 1,1'-{3-[2-(1,2,3,4-tetrahydro-6-methoxy-1-isoquinolinyl)ethyl]heptamethylene}bis[1,2,3,4-tetrahydro-6-methoxyisoquinoline], isolated as its trihydrochloride trihydrate, m.p. 130°-190° (dec.).

When in the above procedure, the m-methoxyphenethylamine is replaced by an equimolar amount of
m-methoxy-β-methylphenethylamine
m-methoxy-α-methylphenethylamine
m-ethoxyphenethylamine
respectively, the following products are obtained:
(10.2): 1,1-{3-[2-(1,2,3,4-tetrahydro-6-methoxy-4-methyl-1-isoquinolinyl)ethyl]heptamethylene}bis[1,2,3,4-tetrahydro-6-methoxy-4-methylisoquinoline] trihydrochloride trihydrate
(10.3): 1,1'-{3-[2-(1,2,3,4-tetrahydro-6-methoxy-3-methyl-1-isoquinolinyl)ethyl]heptamethylene}bis[1,2,3,4-tetrahydro-6-methoxy-3-methylisoquinoline] trihydrochloride trihydrate
(10.4): 1,1'-{3-[2-(6-ethoxy-1,2,3,4-tetrahydro-1-isoquinolinyl)ethyl]heptamethylene}bis[6-ethoxy-1,2,3,4-tetrahydroisoquinoline] trihydrochloride trihydrate Demethylation of the products prepared in Examples 10.1, 1.1 and 1.3 respectively, by the method of Example 4.11, gives rise to the following products:
(10.5): 1,1'-{3-[2-(1,2,3,4-tetrahydro-6-hydroxy-1-isoquinolinyl)ethyl]heptamethylene}bis[1,2,3,4-tetrahydro-6-isoquinolinol] trihydrochloride trihydrate.
(10.6): 1,1'-{3-[2-(1,2,3,4-tetrahydro-6,7-dihydroxy-1-isoquinolinyl)ethyl]heptamethylene}bis[1,2,3,4-tetrahydro-6,7-isoquinolinediol] trihydrochloride trihydrate
(10.7): 1,1'-{3-[2-(1,2,3,4-tetrahydro-6,7,8-trihydroxy-1-isoquinolinyl)ethyl]heptamethylene}bis[1,2,3,4-tetrahydro-6,7,8-isoquinolinetriol] trihydrochloride trihydrate.

Addition of 200 mg. of (10.5) to a mixture of 10 ml. chloroform and 20 ml. acetyl chloride gives rise, after the usual workup, to:
(10.8): 1,1'-{3-[2-(1,2,3,4-tetrahydro-6-hydroxy-1-isoquinolinyl)ethyl]heptamethylene}bis[1,2,3,4-tetrahydro-6-isoquinolinol] triacetate trihydrochloride trihydrate Similarly, when 800 mg. of (10.6) is suspended in 20 ml. glacial acetic acid containing 2 g. of acetyl chloride, and dry hydrogen chloride is bubbled through the mixture, on workup
(10.9): 1,1'-{3-[2-(1,2,3,4-tetrahydro-6,7-dihydroxy-isoquinolinyl)ethyl]heptamethylene}bis[1,2,3,4-tetrahydro-6,7-isoquinolinediol] hexaacetate trihydrochloride trihydrate
is obtained.

EXAMPLE 11

1,1'-{3-[2-(7-BENZYLOXY-1,2,3,4-TETRAHYDRO-6-METHOXY-1-ISOQUINOLINYL)ETHYL]HEPTAMETHYLENE}BIS[7-BENZYLOXY-1,2,3,4-TETRAHYDRO-6-METHOXYISOQUINOLINE] TRIHYDROCHLORIDE

Following the procedure outlined in Example 1, 10 g. of 4-(2-carboxyethyl)nonanedioic acid trimethyl ester on being heated with 26 g. of 4-benzyloxy-3-methoxyphenethylamine yields the corresponding triamide, m.p. 110°-114°, which is cyclized with phosphoric oxychloride (in toluene as solvent), and the resulting product is reduced with sodium borohydride to yield (11.1) 1,1'{3-[2-(7-benzyloxy-1,2,3,4-tetrahydro-6-methoxy-1-isoquinolinyl)ethyl]heptamethylene}bis[7-benzyloxy-1,2,3,4-tetrahydro-6-methoxyisoquinoline], isolated as its trihydrochloride, m.p. 135°-147° (dec.).

Debenzylation of this product by the method of Example 4.9 yields (11.2) 1,1'-{3-[2-(1,2,3,4-tetrahydro-7-hydroxy-6-methoxy-1-isoquinolinyl)ethyl]heptamethylene}bis[1,2,3,4-tetrahydro-6-methoxy7-isoquinolinol] trihydrochloride trihydrate.

Further reaction with butyryl chloride in butyric acid by the method of Example 10.9, gives (11.3) 1,1'-{3-[2-(1,2,3,4-tetrahydro-7-hydroxy-6-methoxy-1-isoquinolinyl)ethyl]heptamethylene}bis[1,2,3,4-tetrahydro-6-methoxy-7-isoquinolinol] tributyrate trihydrochloride trihydrate.

EXAMPLE 12

1-{3,3-BIS[2-(1,2,3,4-TETRAHYDRO-6,7-DIMETHOXY-1-ISOQUINOLINYL)ETHYL]PENTYL)-1,2,3,4-TETRAHYDRO-6,7-DIMETHOXYISOQUINOLINE TRIHYDROCHLORIDE TRIHYDRATE 4-(2-Carboxyethyl)-4-ethylheptanedioic acid trimethyl ester, b.p. 167°-175° 0.5-0.8 mm., is prepared by the Wolff-Kischner reduction of 4-acetyl-4-(2-carboxyethyl)heptanedioic acid followed by esterification of the product with methanol according to the method described in Example 3.

Following the procedure outlined in Example 1, 25 g. of the above triester on being heated with 60 g. of 3,4-dimethoxyphenethylamine yields the corresponding triamide, which, without purification, is cyclized with phosphorus oxychloride, and the product obtained is reduced with sodium borohydride, to yield (12.1) the title compound, m.p. 210°-255° (dec.).

Replacing the 3,4-dimethoxyphenethylamine in the above procedure by an equimolar amount of β-methyl-3,4-methylenedioxyphenethylamine yields (12.2) 1-{3,3-bis[2-(1,2,3,4-tetrahydro-4-methyl-6,7-methylenedioxy-1-isoquinolinyl)ethyl]pentyl}1,2,3,4-tetrahydro-4-methyl-6,7-methylenedioxyisoquinoline], isolated as the trihydrochloride trihydrate.

EXAMPLE 13

1,1'-{3-BENZYL-3-[2-(1,2,3,4-TETRAHYDRO-6,7-DIMETHOXY-1-ISOQUINOLINYL)ETHYL]PENTAMETHYLENE}BIS[1,2,3,4-TETRAHYDRO-6,7-DIMETHOXYISOQUINOLINE] TRIHYDROCHLORIDE TRIHYDRATE

4-Benzyl-4-(2-carboxyethyl)heptanedioic acid trimethyl ester, b.p. 215°-230°/0.4 mm., is prepared by the Wolff-Kishner reduction of 4-benzoyl-4-(2-carboxyethyl)heptanedioic acid, followed by esterification of the product with methanol according to the method described in Example 3.

Following the procedure outlined in Example 1, 80 g. of the above ester on being heated with 200 g. of 3,4-dimethoxyphenethylamine, yields the corresponding triamide which is cyclized with phosphorus oxychloride, and the resulting product is reduced with sodium borohydride to yield (13.1) the title compound, m.p. 155°–180° (dec.).

EXAMPLE 14

1,1'-{3-(p-CHLOROBENZYL)-3-[2-(1,2,3,4-TETRAHYDRO-6,7-DIMETHOXY-1-ISOQUINOLINYL)ETHYL]PENTAMETHYLENE}BIS[1,2,3,4-TETRAHYDRO-6,7-DIMETHOXYISOQUINOLINE] TRIHYDROCHLORIDE 4-(2-Carboxyethyl)-4-(p-chlorobenzyl)heptanedioic acid trimethyl ester, b.p. 270°–280°/0.9 mm., is prepared according to the method outlined in Example 3, starting with 4'-chloroacetophenone, which is cyanoethylated to 3-(p-chlorobenzoyl)-3-(2-cyanoethyl)-1,5-pentanedicarbonitrile, m.p. 135°–137°. On hydrolysis, this trinitrile yields 4-(2-carboxyethyl)-4-(p-chlorobenzoyl)-heptanedioic acid, m.p. 225°–227°, which is subjected to Wolff-Kishner reduction followed by esterification of the product.

Following the procedure outlined in Example 1, 18 g. of the above triester on being heated with 32 g. of 3,4-dimethoxyphenethylamine yields the corresponding triamide which, without purification is cyclized with phosphorus oxychloride, and the resulting product is reduced with sodium borohydride to yield (14.1) the title compound, m.p. 135°–185° (dec.).

By the same sequence of steps, but using in place of the 4'-chloroacetophenone an equimolar amount of
4'-ethoxyacetophenone
3'-trifluoromethylacetophenone
3',4'-methylenedioxyacetophenone
2'-methylacetophenone
3',4'-dimethoxyacetophenone
respectively, the following products are obtained:
(14.2): 1,1'-{3-(p-ethoxybenzyl)-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline] trihydrochloride
(14.3): 1,1'-{3-[2-(1,2,3,4-tetrahydro-6,7-dimethoxy-1-isoquinolinyl)ethyl]-3-(m-trifluoromethylbenzyl)pentamethylene}bis[1,2,3,4-tetrahydro-6,7-dimethoxyisoquinoline] trihydrochloride
(14.4): 1,1'-{3-(3,4-methylenedioxybenzyl)-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline] trihydrochloride
(14.5): 1,1'-{3-(o-methylbenzyl)-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline] trihydrochloride
(14.6): 1,1'-{3-(3,4-dimethoxybenzyl)-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline] trihydrochloride

EXAMPLE 15

1,1',1'',1'''-(1,5,10,14-TETRADECANETETRAYL)-TETRAKIS[1,2,3,4-TETRAHYDRO 6,7-DIMETHOXYISOQUINOLINE] TETRAHYDROCHLORIDE TETRAHYDRATE

To a freshly prepared solution of 13.5 g. of sodium methoxide in 500 ml. of methanol, 55 g. of the mixed methyl and ethyl esters of 1,1'-tetramethylenebis[2-oxocyclohexanecarboxylic acid], b.p. 210°–215°/1 mm., prepared by alkylation of the commercially available mixture of methyl and ethyl 2-oxocyclohexanecarboxylates with 1,4-dibromobutane, are added. The residue is treated with water and extracted twice with 500 ml. portions of ether. The combined ether extracts are washed successively with water, aqueous sodium bicarbonate and water, dried over anhydrous magnesium sulfate and filtered. Removal of the solvent from the filtrate under reduced pressure yields a liquid which is distilled under vacuum. Tetramethyl 1,5,10,14-tetradecanetetracarboxylate, which distills over at 225–235/0.3 mm., solidifies on standing. Trituration with pentane and filtration furnishes colorless crystals, m.p. 61°–65°.

Following the procedure outlined in Example 2, 12.6 g. of the above tetraester on being heated with 21 g. of 3,4-dimethoxyphenethylamine, yields the corresponding tetramide, which is cyclized with phosphorus oxychloride in anhydrous benzene and the resulting product (15.1a) is reduced with sodium borohydride, to yield (15.1) 1,1',1'',1'''-(1,5,10,14-tetradecanetetrayl)tetrakis[1,2,3,4-tetrahydro-6,7-dimethoxyisoquinoline], isolated as its tetrahydrochloride tetrahydrate, m.p. 185°–205° (dec.). The pure dihydro precursor to 15.1, isolated as the colorless solid (15.1a) 1,1',1'',1'''-(1,5,10,14-tetradecanetetrayl)tetrakis[3,4-dihydro-6,7-dimethoxyisoquinoline] tetrahydrochloride tetrahydrate, has a m.p. of 120°–130° (dec.).

When, in the above procedure for the preparation of 15.1, the 3,4-dimethoxyphenethylamine is replaced by an equimolar amount of
m-methoxyphenethylamine
m-methoxy-β-methylphenethylamine
4-benzyloxy-3-methoxyphenethylamine
3-methoxy-4-phenoxyphenethylamine
3-methoxy-2-pentyloxyphenethylamine
3-ethoxy-2-isopentyloxy-1-methylphenthylamine
respectively, the following products are obtained:
(15.2): 1,1',1'',1'''-(1,5,10,14-tetradecanetetrayl)tetrakis[1,2,3,4-tetrahydro-6-methoxyisoquinoline] tetrahydrochloride tetrahydrate
(15.3): 1,1',1'',1'''-(1,5,10,14-tetradecanetetrayl)tetrakis[1,2,3,4-tetrahydro-6-methoxy-4-methylisoquinoline] tetrahydrochloride tetrahydrate
(15.4): 1,1',1'',1'''-(1,5,10,14-tetradecanetetrayl)tetrakis[7-benzyloxy-1,2,3,4-tetrahydro-6-methoxyisoquinoline] tetrahydrochloride tetrahydrate
(15.5): 1,1',1'',1'''-(1,5,10,14-tetradecanetetrayl)tetrakis[1,2,3,4-tetrahydro-6-methoxy-7-phenoxyisoquinoline] tetrahydrochloride tetrahydrate
(15.6)- 1,1',1'',1'''-(1,5,10,14-tetradecanetetrayl)tetrakis[1,2,3,4-tetrahydro-6-methoxy-5-pentyloxyisoquinoline] tetrahydrochloride tetrahydrate
(15.7): 1,1',1'',1'''-(1,5,10,14-tetradecanetetrayl)tetrakis[3-ethoxy-1,2,3,4-tetrahydro-5-isopentyloxy-3-methylisoquinoline] tetrahydrochloride tetrahydrate

EXAMPLE 16

1,1',1'',1'''-(1,4,9,12-DODECANETETRAYL)TETRAKIS[1,2,3,4-TETRAHYDRO-6,7-DIMETHOXYISOQUINOLINE] TETRAHYDROCHLORIDE TETRAHYDRATE

Following the procedure outlined in Example 2, 30 g. of tetramethyl 1,4,9,12-dodecanetetracarboxylate, b.p. 200°–212°/0.5 mm., on being heated with 81.5 g. of 3,4-dimethoxyphenethylamine, yields the corresponding tetramide, m.p. 165°–170°, which is cyclized with phosphorus oxychloride in anhydrous benzene, the product (16.1a) is reduced with sodium borohydride and (16.1) 1,1',1'',1'''-(1,4,9,12-dodecanetetrayl)tetrakis[1,2,3,4-tetrahydro-6,7-dimethoxyisoquinoline] is isolated as its tetrahydrochloride tetrahydrate, m.p. 193°–215° (dec.). Pure (16.1a) 1,1',1'',1'''-(1,4,9,12-dodecanetetrayl)tetrakis[3,4-dihydro-6,7-dimethoxyisoquinoline], isolated as the tetrahydrochloride tetrahydrate, is a light yellow solid which melts at 105°–110° (dec.) after two recrystallizations from isopropanol.

Replacing the 3,4-dimethoxyphenethylamine in the above procedure for the preparation of 16.1, by an equimolar amount of 4-benzyloxy-3-methoxyphenethylamine
m-methoxy-α-methylphenethylamine
3,4,5-trimethoxyphenethylamine
3,4-diethoxyphenethylamine
2-chloro-3,4-dimethoxy-α-methylphenethylamine respectively, yields the following products:
(16.2): 1,1',1'',1'''-(1,4,9,12-dodecanetetrayl)tetrakis[7-benzyloxy-1,2,3,4-tetrahydro-6-methoxyisoquinoline] tetrahydrochloride tetrahydrate
(16.3): 1,1',1'',1'''-(1,4,9,12-dodecanetetrayl)tetrakis[1,2,3,4-tetrahydro-6-methoxy-3-methylisoquinoline] tetrahydrochloride tetrahydrate
(16.4): 1,1',1'',1'''-(1,4,9,12-dodecanetetrayl)tetrakis[1,2,3,4-tetrahydro-6,7,8-trimethoxyisoquinoline] tetrahydrochloride tetrahydrate
(16.5): 1,1',1'',1'''-(1,4,9,12-dodecanetetrayl)tetrakis[6,7-diethoxy-1,2,3,4-tetrahydroisoquinoline] tetrahydrochloride tetrahydrate
(16.6): 1,1',1'',1'''-(1,4,9,12-dodecanetetrayl)tetrakis[5-chloro-1,2,3,4-tetrahydro-6,7-dimethoxyisoquinoline] tetrahydrochloride tetrahydrate

EXAMPLE 17

1,1',1''-[1,2,3-PROPANETRIYLTRI-(OXYETHYLENE)]TRIS[1,2,3,4-TETRAHYDRO-6,7-DIMETHOXYISOQUINOLINE] TRIHYDROCHLORIDE

A mixture of 148 g. of 3,3',3''-(1,2,3-propanetriyltrioxy)tripropionitrile, obtained by the cyanoethylation of glycerol, and 850 ml. of 10% aqueous sodium hydroxide is refluxed overnight, cooled, acidified with conc. hydrochloric acid, and the resulting mixture evaporated to dryness under reduced pressure. Extraction with hot acetone, followed by filtration and removal of the solvent under reduced pressure yields 3,3',3''-(1,2,3-propanetriyltrioxy)tripropionic acid.

A mixture of 46.2 g. of this tripropionic acid and 89 g. of 3,4-dimethoxyphenethylamine is heated at 180°–200° with stirring for five hours under an atmosphere of nitrogen to yield the corresponding triamide, which is cyclized with phosphorus oxychloride in anhydrous benzene to (17.1a) 1,1',1''-[1,2,3-propanetriyltri(oxyethylene)]tris[3,4-dihydro-6,7-dimethoxyisoquinoline], isolated as its trihydrochloride, m.p. 110°–115° (dec.).

On reduction with sodium borohydride, this trihydrochloride yields (17.1) the title compound, isolated as its trihydrochloride, m.p. 205°–210°.

Using the same sequence of steps outlined above for the preparation of 17.1, but using (1,2,3-propanetriyltrioxy)triacetic acid trimethyl ester, obtained by the alkylation of glycerol with methyl chloroacetate, in place of the tripropionic acid, (17.2) 1,1',1''-[1,2,3-propanetriyltri(oxymethylene)]tris[1,2,3,4-tetrahydro-6,7-dimethoxyisoquinoline] is obtained, isolated as its trihydrochloride.

Similarly, but starting with nitrilotripropionic acid, the above sequence of steps yields (17.3) 1,1',1''-(nitrilotriethylene)tris[1,2,3,4-tetrahydro-6,7-dimethoxyisoquinoline], isolated as its trihydrochloride trihydrate, m.p. 175°–185° (dec.).

EXAMPLE 18

1,1'-{3-AMINO-3-[2-(1,2,3,4-TETRAHYDRO-6,7-DIMETHOXY-1-ISOQUINOLINYL)ETHYL]PENTAMETHYLENE}BIS[1,2,3,4-TETRAHYDRO-6,7-DIMETHOXYISOQUINOLINE]

A mixture of 40 g. of 4-(2-carboxyethyl)-4-nitroheptanedioic acid and 250 ml. of pure thionyl chloride is refluxed for 16 hours, and the resulting clear solution is stripped of excess thionyl chloride under reduced pressure. The crude tripropionyl chloride thus obtained is dissolved in 150 ml. of pure chloroform and added, dropwise, to a vigorously stirred mixture of 100 g. of 3,4-dimethoxyphenethylamine in 500 ml. of chloroform and 500 ml. of a 10% aqueous solution of sodium carbonate. On completion of the addition the mixture is stirred for a further 90 minutes, and the chloroform layer is separated. After washing once with water, twice with 6 N hydrochloric acid, and once again with water, it is dried over anhydrous magnesium sulfate and filtered. On removal, under reduced pressure, of the solvent, the corresponding triamide is obtained, which, without purification, is cyclized in phosphorus oxychloride and anhydrous benzene. The resulting product is converted to (18.1a) 1,1'-{3-[2-(3,4-dihydro-6,7-dimethoxy-1-isoquinolinyl)ethyl]-3-nitropentamethylene}·bis[3,4-dihydro-6,7-dimethoxyisoquinoline] trihydrochloride, m.p. 180°–190° (dec.). Reduction of this trihydrochloride with sodium borohydride yields (18.1) 1,1'-{3-nitro-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline], isolated as the trihydrochloride trihydrate, m.p. after recrystallization from isopropanol 210°–220° (dec.).

Reduction of the crude base corresponding to 18.1a with lithium aluminum hydride in anhydrous tetrahydrofuran, followed by purification by chromatography over alumina gives rise to the title compound (18.2), m.p. 85°–115°, which can be converted to a hydrate of a hydrochloride, m.p. 215°–220° (dec.).

EXAMPLE 19

1,1',1''-(1,4,7-HEPTANETRIYL)TRIS[1,2,3,4-TETRAHYDRO-6,7-DIMETHOXYISOQUINOLINE] TRIHYDROCHLORIDE TRIHYDRATE

To a freshly prepared solution of 6.8 g. of sodium ethoxide in 500 ml. of absolute ethanol, 16 g. of the commercially available mixture of methyl and ethyl 2-oxocyclopentanecarboxylates is added with stirring, followed by the addition of 19.9 g. of ethyl 4-bromobutyrate and 2.0 g. of powdered sodium iodide. After the mixture has been refluxed with stirring for 18 hours it is filtered, and the filtrate stripped of the solvent under reduced pressure. The residue is treated with water and extracted twice with 250 ml. portions of ether. The combined ether extracts are washed first with saturated aqueous sodium bicarbonate solution, then with water, and then dried over magnesium sulfate. Filtration and removal of solvent from the filtrate under reduced pressure leaves a liquid, which is distilled under vacuum. The desired triethyl 1,4,7-heptanetricarboxylate is collected at 150°–155°/0.3–0.4 mm.

A mixture of 9.5 g. of this triester and 19.9 g. of 3,4-dimethoxyphenethylamine is heated at 180°–200° for five hours in an atmosphere of nitrogen to yield the corresponding triamide, m.p. 184°–186°, which is cyclized with phosphorus oxychloride in anhydrous benzene to (19.1a) 1,1′,1″-(1,4,7-heptanetriyl)tris[3,4-dihydro-6,7-dimethoxyisoquinoline], isolated as its trihydrochloride by precipitation with ether from a chloroform solution, m.p. 120°–130° (dec.). This trihydrochloride is reduced with sodium borohydride to yield (19.1) the title compound, isolated as its trihydrochloride trihydrate, m.p. 195°–215° (dec.). (sinters at 185°)

EXAMPLE 20

| Ingredients | Mg/Tablet |
| --- | --- |
| 1,1′-3-[2-(1,2,3,4-tetrahydro-6,7-dimethoxy-1-isoquinolinyl)ethyl]heptamethylene bis[1,2,-3,4-tetrahydro-6,7-dimethoxyisoquinoline] trihydrochloride | 25 |
| Lactose USP (Spray dried) | 170 |
| Starch USP | 10 |
| Magnesium stearate USP | 1 |
| Stearic acid USP | 5 |
| Flavor | q.s. |

All of the above ingredients are passed through a 60 mesh sieve, blended for 30 minutes and compressed directly into tablets on a suitable tablet press at a weight of 211 mg. using a 11/32 inch biconcave, scored punch.

EXAMPLE 21

| Ingredients | Ampoule |
| --- | --- |
| 1,1′,1″,1‴-(1,5,10,14-tetradecanetetrayl)-tetrakis[1,2,3,4-tetrahydro-6,7-dimethoxyisoquinoline] tetrahydrochloride | 5 g. |
| Mannitol, N.F. | To make the solution isotonic |
| Pyrogen free water for injection | q.s. to 1 liter |

The compound is added to the water and the solution made isotonic with mannitol. The resulting pH is 5.5. The solution is filled into ampoules under sterile conditions and the sealed ampoule is autoclaved. Each ampoule contains 10 ml. of the 5 mg./ml. solution.

We claim:

1. A compound having formula:

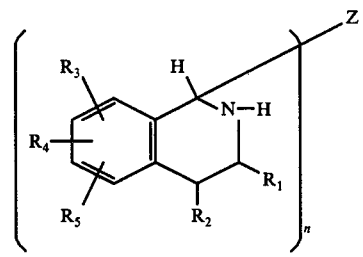

wherein:

$R_1$ and $R_2$ individually represent hydrogen or lower alkyl;

$R_3$, $R_4$, $R_5$ represent hydrogen, lower alkyl, halogen, hydroxy, lower alkoxy, lower alkenoxy, lower alkynoxy, acetoxy, butyryloxy, phenoxy, phenyl lower alkoxy, or $R_3$ and $R_4$ or $R_4$ and $R_5$ may be linked to form methylenedioxy;

$n$ is 3; and

Z is a straight or branched alkanetriyl chain having 5 to 18 carbon atoms which is non-substituted or substituted by a nitro or amino group;

or a pharmaceutically acceptable acid addition salt thereof.

2. The compound of claim 1, 1,1′-{2,2-dimethyl-5-[2-(1,2,3,4-tetrahydro-6,7-dimethoxy-1-isoquinolinyl)ethyl]heptamethylene}-bis[1,2,3,4-tetrahydro-6,7-dimethoxyisoquinoline].

3. The compound of claim 1, 1,1′-{3-[2-(7-benzyloxy-1,2,3,4-tetrahydro-6-methoxy-1-isoquinolinyl)ethyl]heptamethylene}bis[7-benzyloxy-1,2,3,4-tetrahydro-6-methoxyisoquinoline].

4. The compound of claim 1, 1,1′-{3-[2-(1,2,3,4-tetrahydro-7-hydroxy-6-methoxy-1-isoquinolinyl)ethyl]heptamethylene}bis[1,2,3,4-tetrahydro-6-methoxy-7-isoquinolinol].

5. The compound of claim 1, 1,1′-{3-[2-(1,2,3,4-tetrahydro-5,6-dimethyl-1-isoquinolinyl)ethyl]heptamethylene}bis[1,2,3,4-tetrahydro-5,6-dimethylisoquinoline].

6. The compound of claim 1, 1,1′-{3-[2-(6-chloro-1,2,3,4-tetrahydro-1-isoquinolinyl)ethyl]heptamethylene}bis[6-chloro-1,2,3,4-tetrahydroisoquinoline].

7. The compound of claim 1, 1,1′-{3-[2-(1,2,3,4-tetrahydro-6,7-dihydroxyisoquinolinyl)ethyl]heptamethylene}bis[1,2,3,4-tetrahydro-6,7-isoquinolinediol]hexaacetate.

8. The compound of claim 1, 1,1′-{3-[1,2,3,4-tetrahydro-6,7-dimethoxy-4-methyl-1-isoquinolinyl)ethyl]heptamethylene}bis[1,2,3,4-tetrahydro-6,7-dimethoxy-4-methylisoquinoline].

9. The compound of claim 1, 1,1′-{3-[2-(7-allyloxy-1,2,3,4-tetrahydro-6-methoxy-1-isoquinolinyl)ethyl]heptamethylene}bis[7-allyloxy-1,2,3,4-tetrahydro-7-methoxyisoquinoline].

10. The compound of claim 1, 1,1′-{3-[2-(1,2,3,4-tetrahydro-6,7-dimethoxy-1-isoquinolinyl)ethyl]heptamethylene}bis[1,2,3,4-tetrahydro-6,7-dimethoxyisoquinoline].

11. The compound of claim 1, 1,1′-{3-nitro-3-[2-(1,2,3,4-tetrahydro-6,7-dimethoxy-1-isoquinolinyl)ethyl]pentamethylene}bis[1,2,3,4-tetrahydro-6,7-dimethoxyisoquinoline].

12. The compound of claim 1, 1,1′,1″-(1,4,7-heptanetriyl)tris[1,2,3,4-tetrahydro-6,7-dimethoxyisoquinoline].

* * * * *